(12) United States Patent
Gadkari et al.

(10) Patent No.: US 9,072,658 B2
(45) Date of Patent: Jul. 7, 2015

(54) TOOTHPASTE COMPOSITIONS WITH REDUCED ABRASIVITY

(75) Inventors: Vijay Kamalakant Gadkari, Mumbai (IN); Vinayak Bhalchandra Randive, Thane (IN); Mahalingam Ramanan Venkat, Mumbai (IN); Namita Ashok Betrabet, Mumbai (IN); Sitaram Anant Kadam, Mumba (IN)

(73) Assignee: FMC Corporation, Philadelphia, PA (US)

( * ) Notice: Subject to any disclaimer, the term of this patent is extended or adjusted under 35 U.S.C. 154(b) by 1725 days.

(21) Appl. No.: 10/544,282

(22) PCT Filed: Feb. 4, 2004

(86) PCT No.: PCT/US2004/003242
§ 371 (c)(1),
(2), (4) Date: Aug. 7, 2006

(87) PCT Pub. No.: WO2004/071321
PCT Pub. Date: Aug. 26, 2004

(65) Prior Publication Data
US 2007/0009447 A1    Jan. 11, 2007

Related U.S. Application Data

(60) Provisional application No. 60/445,376, filed on Feb. 5, 2003, provisional application No. 60/479,690, filed on Jun. 19, 2003.

(51) Int. Cl.
| | |
|---|---|
| *A61K 8/00* | (2006.01) |
| *A61Q 11/00* | (2006.01) |
| *A61K 8/73* | (2006.01) |
| *A61K 6/00* | (2006.01) |
| *A61K 8/19* | (2006.01) |
| *A61K 8/25* | (2006.01) |

(52) U.S. Cl.
CPC . *A61K 6/00* (2013.01); *A61Q 11/00* (2013.01); *A61K 8/731* (2013.01); *A61K 2800/412* (2013.01); *A61K 8/19* (2013.01); *A61K 2800/5422* (2013.01); *A61K 8/25* (2013.01)

(58) Field of Classification Search
None
See application file for complete search history.

(56) References Cited

U.S. PATENT DOCUMENTS

| | | | |
|---|---|---|---|
| 2,978,446 A | 4/1960 | Battista et al. | |
| 3,539,365 A | 11/1970 | Durand et al. | |
| 4,202,878 A | 5/1980 | Ritze | |
| 4,353,890 A | 10/1982 | Scott | |
| 4,701,319 A | 10/1987 | Woo | |
| 4,980,193 A | 12/1990 | Tuason et al. | |
| 5,094,844 A | 3/1992 | Gaffar et al. | |
| 5,158,764 A | 10/1992 | Again et al. | |
| 5,192,569 A | 3/1993 | McGinley et al. | |
| 5,236,696 A | 8/1993 | Catiis et al. | |
| 5,296,214 A | 3/1994 | Gaffar | |
| 5,366,742 A | 11/1994 | Tuason et al. | |
| 5,601,803 A * | 2/1997 | Masters et al. | 474/49 |
| 5,736,177 A | 4/1998 | McGinley et al. | |
| 5,769,934 A | 6/1998 | Ha et al. | |
| 5,849,267 A | 12/1998 | Collins et al. | |
| 5,939,051 A | 8/1999 | Santalucia et al. | |
| 5,985,323 A | 11/1999 | Augello et al. | |
| 6,025,007 A | 2/2000 | Krawczyk | |
| 6,037,380 A * | 3/2000 | Venables et al. | 514/781 |
| 6,159,446 A | 12/2000 | Randive et al. | |
| 6,162,418 A | 12/2000 | Randive et al. | |
| 6,187,293 B1 | 2/2001 | Ballard | |
| 6,214,320 B1 | 4/2001 | Gaffar et al. | |
| 6,342,205 B1 * | 1/2002 | Niemi et al. | 424/49 |
| 6,391,368 B1 | 5/2002 | Tuason et al. | |
| 2007/0286820 A1 | 12/2007 | Principe et al. | |

FOREIGN PATENT DOCUMENTS

| | | |
|---|---|---|
| EP | 0 319 884 | 12/1988 |
| EP | 0 525 913 A1 | 7/1992 |
| FR | 2625676 A | 7/1989 |
| GB | 1066466 A | 4/1967 |
| GB | 1 271 944 | 4/1972 |
| JP | 9040537 A | 2/1999 |
| JP | 11199456 A | 7/1999 |
| JP | 11246377 A | 9/1999 |
| WO | WO-9534275 A1 | 12/1995 |
| WO | WO-95034275 A1 | 12/1995 |
| WO | WO 99/43291 | 9/1999 |
| WO | WO-00/48561 | 8/2000 |
| WO | WO-03096976 A2 | 11/2003 |
| WO | WO-2004047783 A1 | 6/2004 |
| WO | WO-2007134003 A2 | 11/2007 |

OTHER PUBLICATIONS

Notification of Transmittal of the International Search Report and the Written Opinion of the International Searching Authority, or the Declaration—Dated Mar. 1, 2005—International Application No. PCT/US04/03242.

\* cited by examiner

*Primary Examiner* — Snigdha Maewall
(74) *Attorney, Agent, or Firm* — FMC Corporation

(57) ABSTRACT

Toothpaste compositions are disclosed. The toothpaste composition comprises a binder; a surface active agent; an abrasive; a humectant; and water, in which: (1) the abrasive is silica, the composition additionally comprises a silica thickener, and the composition comprises 1 to 7 wt % of the silica thickener, less than 15 wt % of the silica abrasive, 45 to 70 wt % water, 0.8 to 3.0 wt % of a surface active agent; 0.05 to 3.0 wt % the binder, or (2) the abrasive is silica, the composition additionally comprises a silica thickener, the composition comprises 2 to 22 wt % total silica, 0.8 to 3.0 wt % of a surface active agent; 0.05 to 3.0 wt % the binder, and the composition additionally comprises about 0.1 to 8.0 wt % of non-colloidal microcrystalline cellulose, colloidal microcrystalline cellulose, or a mixture thereof; or (3) the binder is a calcium based abrasive, the binder is a cellulose gum, and the composition comprises 25 to 55 wt % of the calcium based abrasive, 35 to 60 wt % water, 0.8 to 3.0 wt % of the surface active agent, and 1.0 to 3.0 wt % of the binder.

8 Claims, No Drawings

TOOTHPASTE COMPOSITIONS WITH REDUCED ABRASIVITY

CROSS-REFERENCE TO RELATED APPLICATIONS

This application claims priority on U.S. Provisional Patent Application Ser. No. 60/445,376, filed Feb. 5, 2003, incorporated herein by reference, and U.S. Provisional Patent Application Ser. No. 60/479,690, filed Jun. 19, 2003, incorporated herein by reference.

FIELD OF THE INVENTION

This invention relates to toothpaste compositions. More particularly, this invention relates to high moisture toothpaste compositions that have a high moisture content and exhibit reduced abrasivity.

BACKGROUND OF THE INVENTION

For consumer satisfaction, toothpaste compositions should possess certain excellent physical properties to which the consumer is accustomed. These properties provide a toothpaste that has appealing taste, has good cleansing effect, is easy to rinse, has excellent mouth feel, and has physical stability. Toothpaste compositions with acceptable physical stability do not readily harden on the shelf and do not exhibit phase separation such as water or flavor separation. The appearance of the paste as it comes out of the dispenser is also considered important. It should appear smooth and have a pleasant sheen or glossy appearance.

These properties must be provided in a toothpaste composition that is cost effective for the consumer. There is a continuing demand to provide toothpaste compositions at lower cost while maintaining desirable properties. This is especially important in parts of the world where, despite its well-established benefits in dental hygiene, toothpaste is unaffordable.

Toothpaste compositions typically contain a polishing agent or abrasive, a humectant, a binder or thickener, a surface active agent or surfactant, and water, as well as materials that provide therapeutic or cosmetic benefits, such as fluorides, flavorings, and sweeteners. The humectant and water are also referred to collectively as the vehicle. Although the water content varies, most toothpaste compositions comprise about 10 to 25 weight percent water.

Because, compared to the cost of the other ingredients, water is relatively inexpensive, one way to lower the cost of a toothpaste composition is to increase its water content. However, in these toothpaste compositions relatively high water content often produces problems of low viscosity and/or phase separation. During storage water has a tendency to move downward and oils, such flavorings, move upward. With a high moisture toothpaste, the consumer may notice "wet cap" or flavor concentration in the tip depending on whether filled tubes were stored with the caps up or down. Phase separation may also adversely affect the sheen or gloss of the extruded toothpaste composition.

Many conventional toothpaste compositions use silica based polishing agents. However, there is a need in the industry to reduce the abrasive nature of such conventional toothpaste compositions using silica and calcium based polishing agents. Thus, a need exists for a high moisture toothpaste composition with a high moisture content, favorable physical properties, and reduced abrasivity.

SUMMARY OF THE INVENTION

The invention is a toothpaste composition. The toothpaste composition comprises a binder; a surface active agent; an abrasive; a humectant; and water; in which:

(1) the abrasive is silica, the composition additionally comprises a silica thickener, and the composition comprises 1 to 7 wt % of the silica thickener, less than 15 wt % of the silica abrasive, 45 to 70 wt % water, 0.8 to 3.0 wt % of a surface active agent; 0.05 to 3.0 wt % the binder; or (2) the abrasive is silica, the composition additionally comprises a silica thickener, the composition comprises 2 to 22 wt % total silica, 0.8 to 3.0 wt % of a surface active agent; 0.05 to 3.0 wt % the binder, and the composition additionally comprises about 0.1 to 8.0 wt % of non-colloidal microcrystalline cellulose, colloidal microcrystalline cellulose, or a mixture thereof; or (3) the binder is a calcium based abrasive, the binder is a cellulose gum, and the composition comprises 25 to 55 wt % of the calcium based abrasive, 35 to 60 wt % water, 0.8 to 3.0 wt % of the surface active agent, and 1.0 to 3.0 wt % of the binder.

DETAILED DESCRIPTION OF THE INVENTION

Unless the context indicates otherwise, in the specification and claims, the terms abrasive, polishing agent, humectant, binder, microcrystalline cellulose, colloidal microcrystalline cellulose, hydrocolloid, surfactant, surface active agent, flavoring, flavoring agent, sweetener, sweetening agent, antislip agent, attriting agent, and similar terms also include mixtures of such materials. Unless otherwise specified, all percentages are percentages by weight.

Components

The toothpaste compositions comprise an abrasive or polishing agent, a humectant, a binder, a surface active agent, water, and, optionally, other materials that are conventional components of toothpaste compositions, such as flavors and sweeteners. Non-colloidal microcrystalline cellulose, colloidal microcrystalline cellulose, or a mixture thereof, may be present, which reduces the abrasivity of the toothpaste composition.

The solid and liquid components of a toothpaste composition are formulated to produce a product that is an extrudable, creamy material. The binder, or thickener, builds viscosity, provide a desirable consistency and thixotropy, and prevents separation of the ingredients during storage and use. Suitable thickeners include cellulose derivatives ("cellulose gums") such as carboxymethyl cellulose (CMC), methyl cellulose, hydroxyethyl cellulose, hydroxypropyl methyl cellulose, and mixtures thereof; polyvinyl pyrrolidone; xanthan; carrageenans such as iota-carrageenan, kappa-carrageenan, kappa2-carrageenan, lambda-carrageenan, and mixtures thereof; guar gum; gum karaya; gum arabic; gum tragacanth; and mixtures thereof. Carrageenan containing toothpaste is disclosed in Randive, U.S. Pat. No. 6,162,418, incorporated herein by reference. Hydrated silica and colloidal silica may be used as thickeners. Silica thickeners are disclosed, for example, in Niemi, U.S. Pat. No. 6,342,205.

The toothpaste composition comprises an abrasive, which may also be called a polishing agent. Suitable abrasives, or polishing agents, include finely divided water-insoluble powdered materials having no or very low water solubility, typically having a particle size of about 1 to 40 microns in diameter, more typically about 2 to 20 microns in diameter, with normal particle size distributions. These materials have polishing activity without being overly abrasive. Typical abrasives include: calcium-based polishing agents, such as dicalcium phosphate dihydrate (generally known as dicalcium phosphate), tricalcium phosphate, calcium carbonate (such as limestone, natural chalk, or precipitated chalk), calcium pyrophosphate, calcium silicate, and calcium aluminate; magnesium carbonate; magnesium phosphate; sodium metaphosphate; amorphous silica; crystalline silica; precipitated silica; complex aluminosilicate; aluminum hydroxide; aluminosilicates, bentonite, talc, aluminum oxide, silica xerogels, and mixtures thereof. More typical abrasives are dicalcium phosphate, calcium carbonate, and silica.

Non-colloidal microcrystalline cellulose, colloidal microcrystalline cellulose, or a mixture thereof may be added to the toothpaste composition to reduce its abrasivity. These materials reduce the relative amount of abrasive in the toothpaste composition, based on the total solids in the toothpaste composition and, thus, reduces its abrasivity.

Non-colloidal microcrystalline cellulose, typically called microcrystalline cellulose or MCC, is a purified, partially depolymerized cellulose. It may be produced by the hydrolysis procedure described, for example, in Durand, U.S. Pat. No. 3,539,365, and Battista, U.S. Pat. No. 2,978,446. In this procedure, a source of cellulose, preferably alpha-cellulose in the form of a pulp from fibrous plants, is treated with a mineral acid, preferably hydrochloric acid. The resulting crystallite aggregates of microcrystalline cellulose are then separated from the reaction mixture and washed to remove degraded by-products. The resulting wet mass, generally containing 40 to 60 wt % water, is referred to as hydrolyzed cellulose, microcrystalline cellulose, microcrystalline cellulose wetcake, or simply wetcake. The steam explosion process, in which wood chips or other cellulosic materials are placed in a chamber into which super-heated steam is introduced, is disclosed in Ha, U.S. Pat. No. 5,769,934.

Particle size for the non-colloidal microcrystalline cellulose particles is generally less than about 100 microns, typically about 20 microns to about 100 microns. The colloidal microcrystalline cellulose particles have a mean particle size of about 0.1 to about 8 microns, preferably about 0.1 to less than about 1.0 micron, more preferably about 0.1 to about 0.9 micron, and most preferably about 0.1 to about 0.6 micron, as determined by the Horiba Cappa 700 particle size analyzer. Generally, any particle size distribution is acceptable, as long as the mean particle size is within the desired range, and preferably the mean particle size of finely divided microcrystalline cellulose that is substantially colloidal in particle size is less than about 10 microns.

Colloidal microcrystalline cellulose is obtained by reducing the particle size of microcrystalline cellulose and stabilizing the attrited particles to avoid formation of hard aggregates. Techniques for reducing the particle size of microcrystalline cellulose are disclosed in Durand, U.S. Pat. No. 3,539,365; Krawczyk, U.S. Pat. No. 6,025,037; Venables, U.S. Pat. No. 6,037,080, and Tuason, U.S. Pat. No. 6,391,368 and WO 03/09676.

Colloidal microcrystalline cellulose co-processed with a surfactant may be used in the toothpaste compositions. A "surfactant" has a HLB (hydrophilic/lipophilic balance) of about 1 to about 40. Methods for preparing colloidal microcrystalline cellulose co-processed with a surfactant are disclosed, for example, in McGinley, U.S. Pat. No. 5,736,177, and Krawczyk, U.S. Pat. No. 6,025,007. Numerous surfactants are known. Useful surfactants include, for example, lecithin; monoglycerides; mono- and diglycerides; acetylated monoglycerides; ethoxylated monoglycerides; sorbitan esters; sucrose esters; monostearates; monoglyceride or diglyceride esters, including esters of acids such as acetic acid, lactic acid and succinic acid and including diacetyl tartaric acid esters of mono- or diglycerides; propylene glycol monoesters; polyglycerol esters of fatty acids; polysorbates; sodium stearyl lactylate; and ethoxylates, sulfates, and sulfates of ethoxylates of alkyl alcohols in which the alkyl group contains about 8 to about 18 carbon atoms, such as sodium cetyl sulfate, sodium lauryl sulfate (SLS), and disodium lauryl sulfosuccinate. Colloidal microcrystalline cellulose co-processed with sodium stearyl lactylate is commercially available from FMC Corporation as AVICEL® SD 1340.

The co-processed microcrystalline cellulose may contain about 60% to about 95% by weight finely divided microcrystalline cellulose and about 5% to about 40% by weight surfactant co-processed with the cellulose, all percentages based on the total weight of the co-processed material. Preferably, the microcrystalline cellulose comprises about 70 to about 95 wt % of the co-processed material. Preferably, the surfactant comprises about 5 to about 30 wt % of the co-processed material. More preferably, the surfactant comprises about 10 to about 30 wt % of the co-processed material.

Colloidal microcrystalline cellulose co-processed with a hydrocolloid may be used in the toothpaste compositions. Suitable hydrocolloids include, for example, cellulose derivatives such as carboxymethyl cellulose, hydroxypropyl cellulose, hydroxypropyl methyl cellulose, and hydroxyethyl cellulose; gums such as guar, locust bean, gum arabic, xanthan, tragacanth and karaya; seaweed extracts such as kappa-carrageenan, kappa2-carrageenan, iota-carrageenan, lambda-carrageenan, and alginates; and starches such as maltodextrin, hydrolyzed cereal solids, and pectin.

Colloidal microcrystalline cellulose co-processed with carboxymethyl cellulose (CMC), starch, preferably starch having a low amylose content, and a diluent, maltodextrin, whey, or non-fat dry milk solids, preferably maltodextrin, is disclosed in Tuason, U.S. Pat. No. 4,980,193. Colloidal microcrystalline cellulose co-processed with alginate is disclosed in Tuason, U.S. Pat. No. 5,366,742. Colloidal microcrystalline cellulose co-processed with low viscosity alginate complex is disclosed in Augello, U.S. Pat. No. 5,985,323. Colloidal microcrystalline cellulose co-processed with a galactomannan gum, such as locust bean or guar gum, is disclosed in McGinley, U.S. Pat. No. 5,192,569. Colloidal microcrystalline cellulose co-processed with iota-carrageenan is disclosed in Tuason, U.S. Pat. No. 6,391,368. Colloidal microcrystalline cellulose co-processed with sodium carboxymethyl cellulose (MCC/CMC) is available from FMC Corporation as AVICEL® RC-591.

Colloidal microcrystalline cellulose co-processed with a hydrocolloid, such as carrageenan, and a water soluble salt is disclosed in Tuason, WO 03/096976 (PCT/US03/15146), incorporated herein by reference. The co-processed colloidal microcrystalline cellulose is prepared by subjecting a high solids mixture of microcrystalline cellulose and a hydrocolloid to high shear forces in the presence of an antislip agent. Although the antislip agent may be essentially any water soluble salt, salts such as sodium chloride, potassium chloride, calcium lactate, calcium tatrate, calcium citrate, or calcium monophosphate, and especially calcium chloride are preferred antislip agents. The hydrocolloid is added as a dry powder. During processing, it is important that the salt is added before the uniform wetting and swelling of the hydrocolloid powder. The particles have an average particle size less than 10 microns, measured as described above. When the hydrocolloid is carrageenan, at least about 50% of the particles have a particle size less than 3.5 microns. When the hydrocolloid is a hydrocolloid other than carrageenan, at least about 30% of the particles have a particle size less than 3.5 microns. When the hydrocolloid is a combination of carrageenan and another colloid, at least about 20% of the particles have a particle size less than 3.5 microns.

Colloidal microcrystalline cellulose co-processed with both a hydrocolloid and an attriting agent may be used in the toothpaste compositions. Suitable hydrocolloids are listed above. Suitable attriting agents include calcium carbonate (limestone, chalk), dicalcium phosphate, tricalcium phosphate, zinc carbonate, zinc hydroxide, magnesium phosphate, barium carbonate, barium sulfate, ferrous carbonate, aluminum hydroxide, magnesium hydroxide, and magnesium aluminum hydroxide. Other materials useful as attriting aids include silica, various clays, silicates, silicon dioxide, talc, titanium dioxide, and partially soluble organic materials, such as lactose. Preferred attriting agents include calcium carbonate, dicalcium phosphate, and silica, all of which are used as abrasives in toothpaste compositions. Methods for making colloidal microcrystalline cellulose co-processed with a hydrocolloid and an attriting agent are described, for example, in Venable U.S. Pat. No. 6,037,380.

The weight ratio of microcrystalline cellulose to attriting agent is typically about 85:15 to about 30:70, more typically about 70:30 to about 40:60. The hydrocolloid is typically about 5 to 30 wt %, preferably 5% to 15 wt %, of the microcrystalline cellulose; that is, the weight ratio of microcrystalline cellulose to hydrocolloid is about 95:5 to about 70:30.

Equivalent results may be achieved by the use of a mixture of an attriting agent and microcrystalline cellulose co-processed with a hydrocolloid when the particles of attriting agent have the appropriate particle size and the ratio of microcrystalline cellulose and attriting agent falls within the appropriate limits. As described above, the appropriate particle size for the particles of attriting agent is a mean particle size of 0.1 to about 8 microns, preferably about 0.1 to less than about 1.0 micron, more preferably about 0.1 to about 0.9 micron, and most preferably about 0.1 to about 0.6 micron, as determined by the Horiba Cappa 700 particle size analyzer. For the mixture of microcrystalline cellulose and attriting agent, the appropriate weight ratio of microcrystalline cellulose to attriting agent may be about 95:5 microcrystalline cellulose to attriting agent to about 5:95, typically 90:10 to 30:70, more typically 85:15 to about 55:45.

The vehicle of the toothpaste composition is orally acceptable and is comprised of water and a humectant. The humectant provides mouthfeel and also prevents the toothpaste composition from drying out. Typical humectants are polyols of three to six carbons in which each carbon is hydroxylated, and mixtures thereof, such as glycerol (glycerin), sorbitol, polyethylene glycol, polyoxyethylene glycol, mannitol, xylitol, and other sugar alcohols. Sorbitol and glycerol are preferred. The water is preferably deionized and free of impurities.

Toothpaste compositions also comprise a surface active agent to emulsify or otherwise uniformly disperse toothpaste components. The surface active agents are typically anionic or nonionic surface active agents, or mixtures thereof. Examples of suitable surface active agents include water-soluble salts of higher fatty acid monoglyceride monosulfates; higher alkyl sulfates; higher alkyl aryl sulfonates; higher alkyl sulfoacetates; higher fatty acid esters of 1,2 dihydroxy propane sulfonate; substantially saturated higher aliphatic acyl amides of lower aliphatic amino carboxylic acid compounds, such as those having 12 to 16 carbon atoms in the fatty acid, alkyl or acyl radicals; higher olefin sulfonates, higher alkyl poly-lower alkoxy (of 3 to 100 alkoxy groups) sulfates, and fatty acid soaps. Examples of these anionic surface active agents include sodium lauryl sulfate (SLS), sodium hydrogenated coconut oil fatty acids monoglyceride monosulfate, sodium dodecyl benzene sulfonate, sodium lauryl sulfoacetates, sodium N-lauryl sarcosinate, and sodium cocate. Suitable types of nonionic surface active agents include chains of lower alkyene oxides such as ethylene oxide and propylene oxide. A commonly used surface active agent is sodium lauryl sulfate.

The toothpaste composition may comprise a number of other optional ingredients. Agents that provide therapeutic or cosmetic benefits may be present, such as enamel hardening agents, tartar control agents, whitening agents, and antibacterial agents. One or more sweeteners and flavorings may be added for consumer satisfaction. Other materials that are conventional components of toothpaste compositions, such as opacifers and colorants, may also be present.

Examples of flavorings (flavors, flavoring materials, or flavoring agents) include: menthol; carvone; anethole; methyl salicylate; and the oils of spearmint, peppermint, wintergreen, sassafras, clove, sage, eucalyptus, marjoram, cinnamon, lemon, lime, grapefruit, kumquat, tangerine, and orange. Examples of sweeteners (sweetening agents) include sucrose, lactose, maltose, sorbitol, xylitol, sodium cyclamate, perillartine, L-aspartyl-L-phenylalanine methyl ester (aspartame), and saccharine. Pyrophosphate salts having anti-tartar efficacy such as a dialkali or tetra-alkali metal pyrophosphate salts such as $Na_4P_2O_7$ (TSPP), $K_4P_2O_7$, $Na_2K_2P_2O_7$, $Na_2K_2H_2O_7$, and $K_2H_2P_2O_7$, long chain polyphosphates such as sodium hexametaphosphate, and cyclic phosphates such as sodium trimetaphosphate may be present in the toothpaste composition. Examples of hardening agents are fluoride salts such as sodium fluoride, potassium fluoride, calcium fluoride, zinc fluoride, stannous fluoride, zinc ammonium fluoride, sodium monofluorophosphate, potassium monofluorophosphate, and laurylamine hydrofluoride.

Antibacterial agents may also be included in the toothpaste compositions. Especially useful are non-cationic antibacterial agents that are based on phenolic and bisphenolic compounds, halogenated diphenyl ether, benzoate esters and carbanilides, such as sodium benzoate; 4-chlorophenol, 2,2'-trichloro-2-hydroxy-diphenyl ether (triclosan); esters of p-hydroxybenzoic acid, especially the methyl, ethyl (ethyl parasept), propyl (propyl parasept), butyl (butyl parasept), and benzyl esters; 3,4,4'-trichlorocarbanalide and 3,3',4-trichlorocarbanilide. A preferred antimicrobial agent is triclosan. Nonionic antimicrobial agents such as sesquiterpene alcohols such as merolidol and bisabolol are also useful.

Whitening agents may be present in the toothpaste composition. Useful whitening agents are oxidizing agents such as calcium peroxide, urea peroxide, peracetic acid, and sodium percarbonate. An opacifier, such as titanium dioxide, may be added to make the toothpaste opaque or to increase its opacity.

The toothpaste composition may also comprise other ingredients that are conventional components of toothpaste compositions, including, for example, desensitizing agents for sensitive teeth such as sodium nitrate; orally acceptable colorants such beta-carotene, chlorophyllin, FD&C Yellow #5, FD&C Yellow #6, FD&C Blue #2, FD&C Red #4, FD&C Green #6, FD&C Yellow #10, FD&C Red #40, D&C Green #5, D&C Red #30 lake, and FD&C Blue #1 lake; healing agents, such as rose-seed oil; chelating/sequestering agents, such as citrates; vitamins, such as vitamin C and vitamin E; amino acids; proteins; antibiotics; anti-enzymes; enzymes; pH control agents (buffers); antioxidants; and preservatives.

Composition

The toothpaste composition typically comprises about 0.05 to 3.0 wt % of the binder, based on the total weight of the toothpaste composition. When carrageenan or xanthan is used as the binder, less binder is typically required than when a cellulose derivative such as carboxymethyl cellulose is used as the binder. When a cellulose derivative such as carboxymethyl cellulose is used as the binder, the binder typically comprises about 0.25 to about 3.0 wt % and preferably about 1.0 to about 1.5 wt % of the toothpaste composition. When carrageenan or a mixture of carrageenan is used as the binder, the binder typically comprises about 0.05 to 2.5 wt % of carrageenan. Processes for preparing low carrageenan toothpastes are disclosed in Ballard, U.S. Pat. No. 6,187,293, incorporated herein by reference.

The toothpaste compositions of the invention are high moisture toothpastes. The amount of water present in a "high moisture toothpaste composition" depends to some extent of the abrasive used in the toothpaste composition. Higher levels of calcium based abrasives, such as dicalcium phosphate and calcium carbonate, and lower levels of silica are used in toothpaste compositions. Therefore, a silica-based high moisture toothpaste composition will typically comprise more water than one that comprises a calcium based abrasive. High moisture toothpastes that comprise iota-carrageenan as the binder, and their preparation, are described, for example, in Randive, U.S. Pat. No. 6,159,446, incorporated herein by reference.

Two types of silica may be used in a toothpaste composition. Silica is used as abrasive. Examples are ZEODENT® 113, ZEODENT® 115, ZEODENT® 124, and ZEODENT® 623 (J.M. Huber Co., Edison, N.J. USA). Silica is also used as a thickener. Examples are ZEODENT® 165, ZEODENT® 163, and ZEODENT® 153 (J.M. Huber Co., Edison, N.J. USA). The difference in properties between these two types of materials is given in Niemi, U.S. Pat. No. 6,342,202, especially in Tables B and C, and accompanying disclosure. The disclosure of U.S. Pat. No. 6,342,202, is incorporated herein by reference.

It has been discovered high moisture toothpastes can be prepared that contain less than 8%, typically 7 wt % or less, more typically 1 to 7 wt %, of silica thickener. This toothpaste composition has less abrasivity than toothpaste compositions that comprise 8 wt % to 15 wt % silica thickener. In addition, the toothpaste composition comprises less that 15%, 1 to less than 15 wt %, in some cases 6 to 10 wt %, of silica abrasive. The total amount of silica present is 2 to 22 wt %, in some cases 8 to 18 wt %, and in other cases 10 to 14% of total silica.

The abrasivity of a silica containing toothpaste composition, including but not limited to, the high moisture silica containing toothpaste compositions described above, is reduced by microcrystalline cellulose. When present, about 0.1 to 8.0% wt %, typically about 0.2 to 4 wt %, more typically about 0.3 to 2.0 wt % and 0.4 to 1.6 wt %, based on the total weight of the toothpaste composition, of non-colloidal microcrystalline cellulose, colloidal microcrystalline cellulose, or a mixture thereof, is present in the toothpaste composition. This reduces the relative amount of abrasive in the toothpaste composition, based on the total solids in the toothpaste composition and, thus, reduces its abrasivity.

Water comprises 45 to 70 wt % of the high moisture silica containing toothpaste composition. The water content may 50 to 70 wt % and 60 to 70 wt %, based on the total weigh of the toothpaste composition.

The "as made" viscosity (i.e., the viscosity of the composition after cooling to ambient temperature but before standing for more than several hours or the "initial viscosity") of the silica abrasive containing high moisture toothpaste composition is typically less than 200,000 cp. The viscosity of the toothpaste composition as made is typically in the range of about 80,000 to 180,000 cp, more typically, about 100,000 to 165,000 cp, even more typically about 120,000 to 155,000 cp. This range is convenient for use in automated filling equipment.

When dicalcium phosphate (DCP) is used as the abrasive, the toothpaste composition typically comprises about 25 to 55 wt %, more typically about 35 to 53 wt % of dicalcium phosphate. When calcium carbonate is used as the abrasive, the composition typically comprises about 25 to 55 wt %, more typically about 35 to 50 wt %, of calcium carbonate. Thus, because of higher level of abrasive, the amount of water in these high moisture toothpaste compositions will be less than in one that contains silica. These high moisture toothpaste compositions contain 35 to 60 wt % water, preferably 40 to 60 wt % water. The binder is a cellulose gum, preferably carboxymethyl cellulose, typically about 1.0 to 3.0 wt %. The amount of binder may be reduced by the presence of a silica thickener, for example up to about 7 wt %, such as 1.0 to 7.0 wt %, typically about 1.0 to 4.0 wt % of a silica thickener, or by the presence of silica thickener and microcrystalline cellulose, for example, 0.5 to 7.0 wt %, typically 0.5 to 2.0 wt % of the silica thickener and 0.5 to 10.0 wt %, typically 1.0 to 3.0 wt % of the non-colloidal microcrystalline cellulose, colloidal microcrystalline cellulose, or a mixture thereof.

After the abrasive, the water, the binder, and the other ingredients, have been accounted for, humectant accounts for the balance of the material. Typically, as the amount of water is increased, the amount of humectant in the toothpaste composition decreases. The toothpaste composition comprises about 8 to 45 wt % humectant, typically about 10 to 25 wt % on an absolute basis. Toothpaste compositions that comprise 10 to 15 wt % of humectant, on an absolute basis, have been prepared. Sorbitol, for example, is commercially available as 70% sorbitol/30% water mixture. "On an absolute basis" means the amount of humectant, exclusive of any water that is present in the humectant.

The toothpaste composition typically comprises about 0.8 to about 3.0 wt %, preferably about 1.0 to about 2.0 wt %, of the surface active agent. When a flavoring is present, the toothpaste composition typically comprises about 0.1 to about 2.0 wt %, more typically about 0.5 to about 1.5 wt %, of the flavoring. When a sweetener is present, the toothpaste composition typically comprises about 0.1 to about 2 wt % of the sweetener. When an anti-tartar agent is present, the toothpaste composition typically comprises about 0.5% to about 8.0 wt % of the anti-tarter agent. When an anti-bacterial agent is present, the toothpaste composition typically comprises about 0.03 to about 1 wt % of the antibacterial agent. When a whitening agent is present, the toothpaste composition typically comprises about 0.1 to about 5 wt %, preferably about 0.5 to about 2 wt %, of the whitening agent. When a pyrophosphate salt is present, the toothpaste composition typically comprises about 0.5 to about 8.0 wt %, preferably about 1.5 to about 3 wt %, of the pyrophosphate salt. When a hardening agent is present, it typically comprises about 0.1 to about 5 wt % of the toothpaste composition. When present, other ingredients, such as dyes and opacifiers, are present in effective amounts, that is, each ingredient is present in the amount necessary to achieve its particular purpose.

Toothpaste Preparation

The toothpaste compositions can be prepared using either the hot process or the ambient process, and either a batch process or a continuous process may be used. The ambient process is sometimes called the cold process. The hot process is described, for example, in Scott, U.S. Pat. No. 4,353,890, and Ballard, U.S. Pat. No. 6,187,293, the disclosures of which are incorporated herein by reference. A continuous process for the manufacture of toothpaste is disclosed, for example, in Ballard, U.S. Pat. No. 6,187,293, especially in FIG. 1 and the accompanying text, the disclosure of which is incorporated herein by reference. A continuous process for the manufacture of toothpaste is also disclosed in Catiis, U.S. Pat. No. 5,236,696. An example of the hot process that can be used to prepare the toothpaste compositions is given in the Examples. The ambient process is the same as the hot process, except that steps (2) and (3) of the process given in the Examples are carried out at about 25° C.

Industrial Applicability

The toothpaste compositions of the invention are useful in oral hygiene.

The advantageous properties of this invention can be observed by reference to the following examples, which illustrate but do not limit the invention.

EXAMPLES

| Glossary | |
|---|---|
| AVICEL ® CL 611 | Colloidal microcrystalline cellulose and sodium carboxymethylcellulose in ratio of 85/15, by weight (FMC, Philadelphia, PA USA) |
| AVICEL ® PH 102 | Non-colloidal microcrystalline cellulose (FMC, Philadelphia, PA USA) |
| AVICEL ® PH 105 | Non-colloidal microcrystalline cellulose (FMC, Philadelphia, PA USA) |
| AVICEL ® RC-591 | Colloidal microcrystalline cellulose co-processed with sodium carboxymethyl cellulose in a ratio of 89/11, by weight (FMC, Philadelphia, PA USA) |
| CMC | Commercial medium viscosity grade of carboxymethylcellulose |
| DCP | Dicalcium phosphate dihydrate, commonly called dicalcium phosphate |
| MCC | AVICEL ® PH 101; Non colloidal microcrystalline cellulose powder having an average particle size of 50 to 100 microns (FMC, Philadelphia, PA USA) |
| MCC/CMC | AVICEL ® RC-591 colloidal microcrystalline cellulose co-processed with sodium carboxymethyl cellulose (FMC, Philadelphia, PA USA) |
| MCC/SLS | Colloidal microcrystalline cellulose co-processed with sodium lauryl sulfate |
| MCC/CMC/ CaCO$_3$ | Colloidal microcrystalline cellulose co-processed with carboxymethyl cellulose and calcium carbonate |
| SLS | Sodium lauryl sulfate |
| SMFP | Sodium mono-fluorophosphate |
| TP 399 | Binder containing primarily a mixture of iota-carrageenans; Brookfield viscosity 20 to 50 cp (measured at 1.5% solids in deionized water at 75° C.) (FMC, Philadelphia, PA USA) |
| ZEODENT ® 113 | Amorphous silica used as an abrasive (J.M. Huber, Edison NJ USA) |
| ZEODENT ® 165 | Amorphous silica used as a thickener (J.M. Huber, Edison NJ USA) |

General Procedures

Materials

In the examples in which sorbitol was used, the sorbitol was a 70% solution in water so the moisture content of the toothpaste composition is equal to the total amount of water shown in the Table plus the 30% water in the sorbitol.

Sample Preparation

The toothpaste compositions were prepared using the hot process by the following procedure:

(1) The binder and the colloidal microcrystalline cellulose are dispersed into the humectant with a high-speed stirrer and stirred, for example, for about 10 minutes to form a gel.

(2) The water can then be heated to about 80° C. and added to the humectant and binder/colloidal microcrystalline cellulose mixture with stirring continuing for 15 minutes while the temperature is maintained at 60-70° C.

(3) The dry ingredients, such as sodium saccharin, sodium benzoate, etc, exclusive of the abrasive are dry blended. The dry blend is stirred into the binder slurry and stirred for 15 minutes while the temperature is maintained at 60-70° C.

(4) The resulting gel (elixir) is transferred to a low speed Ross™ mixer with a vacuum attachment. The Ross™ mixer is a double planetary gear, two-paddle mixer, which operates at 20 to 100 revolutions per minute and can be operated under vacuum.

(5) The abrasive (polishing agent) is added sequentially to the elixir and mixed for 15 minutes under vacuum (at least 720 mm Hg.).

(6) Flavoring is added to the elixir and mixed for 10 minutes in the Ross mixer under full vacuum.

(7) The surfactant, such as sodium lauryl sulfate (SLS), is added to the mix and mixing is continued under vacuum for 20 minutes.

(8) A sample is withdrawn for testing, and the batch is discharged for filling tubes or other dispensers.

Viscosity Measurement

Toothpaste composition viscosity was measured with a T-E spindle at 5 rpm using a Brookfield DVII Viscometer equipped with a Helipath attachment as follows: the sample was equilibrated at ambient temperature (23° C.) in Method A and 25° C. in Method B. Viscosity was measured by placing the spindle directly into the tube containing 30-40 gm of the toothpaste composition as per Method A and allowing the spindle to penetrate into the paste in the tube as per Method B.

Method A: The stationary spindle was positioned within the sample. The viscometer was turned on and readings were recorded every 10 seconds for 1 minute for a total of six readings, which were then averaged.

Method B: The spindle was positioned slightly above the sample surface and allowed to move down the Helipath to enter the sample. The reading was observed to initially increase as the spindle moved further into the sample. The sample viscosity was recorded when a stable reading was obtained while the spindle was still moving downward within 30 seconds.

Cuban Test

In the Cuban test (also termed the "Rack" test), the paste is squeezed from a tube through a fixed orifice across a grid of parallel rods, increasingly spaced apart. The test results are expressed as the greatest space number (numbers are from 1-12) which represents the longest distance between rods that support the dentifrice ribbon without having it break. The rack is about 300 millimeters (mm) long and about 100 mm wide. The stainless steel rods are spaced at increasing distances apart starting at 3 mm between rods 1 and 2 (space number 1) and the distance between rods increases by 3 mm from rod to rod. Thus the distance between rods 2 and 3 is 6 mm, and the distance between the twelfth and thirteenth rod (space number 12) is 39 mm. For toothpastes that are not high moisture toothpastes, ratings of 1-2 and 9-12 are not acceptable, 3 and 8 are acceptable, 4-7 are good.

To carry out the Cuban test, the following procedure is followed:

(1) A nozzle is fixed to a toothpaste tube filled with a toothpaste composition to be tested.

(2) The tube filled with test toothpaste composition and having the nozzle attached is held at an angle of 45° to the rack device. Pressure is applied at the bottom of the tube and a uniform ribbon of paste is squeezed from the tube. While the ribbon of paste is being extruded from the tube the tube is moved across the rack in a straight line. The time to stretch the ribbon of paste over the rack is usually about two to four seconds. If the ribbon breaks before the entire rack is traversed, the procedure is repeated.

(3) The ribbon is allowed to stand for 30 seconds. At that time, the point at which the ribbon breaks is recorded as the rack rating or Cuban value.

(4) The test is performed five times and the average reading is recorded, rounding off to the nearest complete figure.

Examples 1 to 3 and Comparative Examples 1 and 2

These examples show that microcrystalline cellulose produces a toothpaste composition with a higher water content and excellent storage stability. Comparative Example 1 is a standard toothpaste formulation based on dicalcium phosphate polishing agent (DCP) and carrageenan binder. It has a lower water content and no microcrystalline cellulose. Comparative Example 2 has less dicalcium phosphate but no microcrystalline cellulose. Examples 1 to 3 have less dicalcium phosphate and contain microcrystalline cellulose.

TABLE 1

TOOTHPASTES CONTAINING CARRAGEENAN AND MCC

| Ingredient | Comp. Ex. 1 Std DCP | Comp. Ex. 2 Low DCP | Ex. 1 Low DCP | Ex. 2 Low DCP | Ex 3 Low DCP |
|---|---|---|---|---|---|
| Glycerin | 22.00 | 22.00 | 22.00 | 22.00 | 22.00 |
| TP-399 | 0.80 | 1.30 | 1.00 | 0.85 | 1.00 |
| Sodium benzoate | 0.50 | 0.50 | 0.50 | 0.50 | 0.50 |
| Saccharin | 0.15 | 0.15 | 0.15 | 0.15 | 0.15 |
| SMFP | 0.76 | 0.76 | 0.76 | 0.76 | 0.76 |
| DCP | 52.00 | 35.00 | 35.00 | 35.00 | 25.00 |
| ZEODENT ® 165 | 0 | 0 | 0 | 0 | 5.00 |
| MCC | 0 | 0 | 1.00 | 7.00 | 2.00 |
| Flavoring | 0.90 | 0.90 | 0.90 | 0.90 | 0.90 |
| SLS | 1.50 | 1.50 | 1.50 | 1.50 | 1.50 |
| Water[a] | 21.39 | 37.89 | 37.19 | 31.34 | 41.19 |

[a]The same as the Moisture Content

TABLE 2

TOOTHPASTES CONTAINING CARRAGEENAN AND MCC

| Storage Stability | Comp. Ex. 1 Std DCP | Comp. Ex. 2 Low DCP | Ex. 1 Low DCP | Ex. 2 Low DCP | Ex 3 Low DCP |
|---|---|---|---|---|---|
| 25° C. Initial | | | | | |
| Cubans[a] | 5 | 7 | 5 | 5 | 5 |
| Cp | ND | 155,000 | 169,000 | ND | 115,000 |
| 1 Day | | | | | |
| Cubans | 5 | 5 | 4 | 5 | 5 |
| 3 Weeks | | | | | |
| Cubans | ND | 5 | 4 | ND | 5 |
| 6 Weeks | | | | | |
| Cubans | ND | 5 | 4 | ND | 5 |
| 12 Weeks | | | | | |
| cp/Cubans | 5 | 5 | 3 | 5 | 4 |
| cp[b] | ND | 141,000 | 89,000 | ND | 129,000 |
| Appearance | Good | Good | Thin | Good | Good |
| 6 Months | | | | | |
| Cubans | 5 | 5 | 2 | 5 | 3 |
| Appearance | Good | Good | Thin | Good | Thin |
| 1 Year | | | | | |
| Cubans | 5 | ND | ND | 4 | ND |
| Appearance | Good | ND | ND | Good | ND |
| 50° C. 3 Weeks | | | | | |
| Cubans | ND | 5 | 4 | ND | 4 |
| 6 Weeks | | | | | |
| Cubans | ND | 5 | 4 | ND | 4 |
| 12 Weeks | | | | | |
| Cubans | 6 | 5 | 3 | 5 | 5 |
| Cp | ND | 131,000 | 88,000 | ND | 129,000 |
| Appearance | Good | Good | Thin | Good | Good |

ND = Not Determined
[a]Viscosity of the toothpaste composition in Cubans.
[b]Viscosity of the toothpaste composition in cp.

Comparative Example 2 shows that the viscosity decreased from seven Cubans to five Cubans in one day for a less abrasive, higher water content toothpaste that does not comprise microcrystalline cellulose. Examples 1 to 3 show that formulations containing microcrystalline cellulose produce low abrasion toothpaste compositions having both the higher water content and excellent long term stability.

Similar results are obtained when a 50:50 mixture of MCC/CMC/CaCO$_3$ and MCC is used in place of the MCC in Examples 1, 2, and 3.

Examples 4 and 5 and Comparative Example 3

This example demonstrates the ability to formulate higher moisture content silica toothpaste compositions with microcrystalline cellulose. The toothpaste compositions shown in Table 3 were prepared as described above. The results are given in Table 4.

TABLE 3

SILICA-BASED TOOTHPASTES CONTAINING CARRAGEENAN AND MCC

| Ingredient | Comp. Ex 3 Std Silica | Example 4 | Example 5 |
|---|---|---|---|
| 70% Sorbitol | 68.00 | 35.00 | 35.00 |
| TP-399 | 0.50 | 1.00 | 1.00 |
| Sodium benzoate | 0.20 | 0.20 | 0.20 |
| Saccharin | 0.20 | 0.20 | 0.20 |
| ZEODENT ® 165 | 7.00 | 7.00 | 7.00 |
| ZEODENT ® 113 | 11.00 | 11.00 | 11.00 |
| MCC | 0 | 2.00 | 4.00 |
| Flavoring | 1.00 | 1.00 | 1.00 |
| SLS | 2.00 | 2.00 | 2.00 |

TABLE 3-continued

SILICA-BASED TOOTHPASTES CONTAINING CARRAGEENAN AND MCC

| Ingredient | Comp. Ex 3 Std Silica | Example 4 | Example 5 |
|---|---|---|---|
| Water | 10.10 | 40.60 | 38.60 |
| Moisture Content | 30.5 | 51.1 | 49.1 |

TABLE 4

SILICA-BASED TOOTHPASTES CONTAINING CARRAGEENAN AND MCC

| Storage Stability | Comp. Ex. 3 Std Silica | Example 4 | Example 5 |
|---|---|---|---|
| 25° C. Initial | | | |
| Cubans[a] 1 Day | 4 | 2 | 2 |
| Cubans 12 Weeks | 4 | 3 | 3 |
| Cubans Appearance 6 Months | 5 Good | 7 Good | 8 Good |
| Cubans Appearance 50° C. 12 Weeks | 4 Good | 5 Good | 5 Good |
| Cubans Appearance | 5 Good | 7 Good | 8 Good |

Similar results are obtained when a 50:50 mixture of MCC/CMC/CaCO$_3$ and MCC is used in place of the MCC in Examples 4 and 5.

Example 6 and 7 and Comparative Example 4

This example demonstrates the ability to formulate higher moisture content silica toothpaste compositions with microcrystalline cellulose. The toothpaste compositions shown in Table 5 were prepared as described above. The results are given in Table 6.

TABLE 5

SILICA-BASED TOOTHPASTES CONTAINING CARRAGEENAN AND MCC

| Ingredient | Comp. Ex 4 Std Silica | Example 5 | Example 6 |
|---|---|---|---|
| 70% Sorbitol | 68.00 | 30.00 | 30.00 |
| TP-399 | 0.80 | 1.00 | 0.70 |
| Sodium benzoate | 0.20 | 0.20 | 0.20 |
| Saccharin | 0.20 | 0.20 | 0.20 |
| ZEODENT ® 165 | 7.00 | 7.00 | 7.00 |
| ZEODENT ® 113 | 11.00 | 7.00 | 7.00 |
| MCC | 0. | 0 | 1.00 |
| Flavoring | 0.90 | 1.00 | 1.00 |
| SLS | 2.00 | 2.00 | 2.00 |
| Water | 9.80 | 51.6 | 50.9 |
| Moisture Content | 30.2 | 60.6 | 59.9 |
| Viscosity | | | |
| Initial cp/Cubans | ND/55 | 156,000/65 | 110,000/44 |
| 1 day | 5 | 5 | 4 |

The toothpaste compositions of Examples 5 and 6 are high moisture compositions that comprise of 14% silica.

Examples 8 and 9 and Comparative Example 5

This example demonstrates the ability to formulate high moisture silica toothpaste compositions with microcrystalline cellulose. The toothpaste compositions shown in Table 6 were prepared as described above.

TABLE 6

SILICA-BASED TOOTHPASTES CONTAINING CMC AND MCC

| Ingredient | Comp. Ex. 6 Std silica | Example 8 | Example 9 |
|---|---|---|---|
| 70% Sorbitol | 68.00 | 17.00 | 17.00 |
| CMC | 0.80 | 1.10 | 1.10 |
| Sodium benzoate | 0.20 | 0.50 | 0.50 |
| Saccharin | 0.20 | 0.10 | 0.10 |
| ZEODENT ® 165 | 7.00 | 10.00 | 10.00 |
| ZEODENT ® 113 | 11.00 | 10.00 | 10.00 |
| MCC | 0 | 0 | 2.00 |
| Flavoring | 0.90 | 0.50 | 0.50 |
| SLS | 2.00 | 0.80 | 0.80 |
| Water | 9.80 | 60.00 | 58.0 |
| Moisture Content | 30.2 | 65.1 | 63.1 |
| Storage Stability Room Temperature Initial | | | |
| Cubans[a] 1 Day | 1 | 2 | 2 |
| Cubans 12 Weeks | 2 | 3 | 3 |
| Cubans Appearance 6 Months | 4 Good | 5 Good | 5 Good |
| Cubans Appearance 50° C. 12 Weeks | 5 Good | 5 Good | 5 Good |
| Cubans Appearance | 5 Good | 7 Good | 8 Good |

[a]Viscosity of the toothpaste composition in Cubans.

Examples 10 to 15

These examples show that a variety of binders may be used in the toothpaste compositions of the invention. The following toothpaste compositions were prepared and evaluated as described above. Examples 10 to 15 are toothpaste compositions that contain carrageen, carboxymethyl cellulose, or xanthan/carboxymethyl cellulose, respectively, as the binder, in addition to microcrystalline cellulose. Examples 10, 12, and 14 also contain microcrystalline cellulose.

TABLE 7

SILICA-BASED TOOTHPASTES CONTAINING CARAGEENAN/CMC

| Ingredient | Example 10 | Example 11 |
|---|---|---|
| 60:40 TP-399/CMC | 1.00 | 1.00 |
| 70% Sorbitol | 28.00 | 28.00 |
| Sodium benzoate | 0.20 | 0.20 |
| Saccharin | 0.20 | 0.20 |
| ZEODENT ® 165 | 7.00 | 7.00 |
| ZEODENT ® 113 | 11.00 | 11.00 |

TABLE 7-continued

SILICA-BASED TOOTHPASTES CONTAINING CARAGEENAN/CMC

|  | Example 10 | Example 11 |
|---|---|---|
| MCC | 1.00 | 0 |
| Flavoring | 1.00 | 1.00 |
| SLS | 2.00 | 2.00 |
| Water | 48.6 | 49.6 |
| Moisture Content | 57.0 | 58.0 |
| Viscosity |  |  |
| Initial cp/Cubans | ND | 202,000/5 |
| 1 day | ND | ND |

TABLE 8

SILICA-BASED TOOTHPASTES CONTAINING CMC

|  | Example 12 | Example 13 |
|---|---|---|
| Ingredient |  |  |
| CMC | 1.50 | 1.50 |
| Sorbitol | 28.00 | 28.00 |
| Sodium benzoate | 0.20 | 0.20 |
| Saccharin | 0.20 | 0.20 |
| ZEODENT ® 165 | 7.00 | 7.00 |
| ZEODENT ® 113 | 11.00 | 11.00 |
| MCC | 2.00 | 0 |
| Flavoring | 1.00 | 1.00 |
| SLS | 2.00 | 2.00 |
| Water | 47.1 | 49.1 |
| Moisture Content | 55.5 | 57.5 |
| Viscosity |  |  |
| Initial cp/Cubans | 101,000/2 | 84,000/2 |
| 1 day Cubans | 3 | 2 |

TABLE 9

SILICA-BASED TOOTHPASTES CONTAINING XANTHAN/CMC

|  | Example 14 | Example 15 |
|---|---|---|
| Ingredient |  |  |
| 60:40 Xanthan/CMC | 1.30 | 1.30 |
| Sorbitol | 28.00 | 28.00 |
| Sodium benzoate | 0.20 | 0.20 |
| Saccharin | 0.20 | 0.20 |
| ZEODENT ® 165 | 7.00 | 7.00 |
| ZEODENT ® 113 | 11.00 | 11.00 |
| MCC | 1.00 | 0 |
| Flavoring | 1.00 | 1.00 |
| SLS | 2.00 | 2.00 |
| Water | 48.3 | 49.3 |
| Moisture Content | 56.7 | 57.7 |
| Viscosity |  |  |
| Initial cp/Cubans | 86,000/3 | 80,000/3 |
| 1 day Cubans | 4 | 3 |

Example 16 to 18

These examples illustrate the use of microcrystalline cellulose and co-processed colloidal microcrystalline cellulose in high moisture toothpaste compositions. Using the procedures described above, the toothpaste compositions shown in Table 10 were prepared and evaluated.

TABLE 10

HIGH MOISTURE TOOTHPASTE COMPOSITIONS

|  | Example 16 | Example 17 | Example 18 |
|---|---|---|---|
| Ingredient |  |  |  |
| TP 399 | 0.70 | 0.70 | 0.70 |
| 70% Sorbitol | 15.00 | 15.00 | 15.00 |
| Sodium Saccharin | 0.20 | 0.20 | 0.20 |
| Methyl paraben | 0.08 | 0.08 | 0.08 |
| Propyl paraben | 0.02 | 0.02 | 0.02 |
| ZEODENT ® 165 | 7.00 | 7.00 | 7.00 |
| ZEODENT ® 113 | 9.00 | 9.00 | 9.00 |
| AVICEL ® PH 105 | 0.50 | 0 | 0 |
| AVICEL ® CL 611 | 0 | 0.50 | 0 |
| AVICEL ® RC 591 | 0 | 0 | 0.50 |
| Flavoring | 1.00 | 1.00 | 1.00 |
| SLS | 2.00 | 2.00 | 2.00 |
| Water | 64.50 | 64.50 | 64.50 |
| Moisture Content | 69.0 | 69.0 | 69.0 |
| Viscosity (Initial) cps/Cuban | 120,000/5 | 124,000/6 | 146,000/7 |
| Viscosity (1 Day) cps/Cuban | 127,000/5 | 141,000/7 | 158,000/7 |
| Stability (12 weeks - 25° C.) |  |  |  |
| Viscosity cps/Cuban | 121,000/6 | 126,000/6 | 142,000/6 |

Example 19

This example illustrates the use of colloidal microcrystalline cellulose co-processed with a hydrocolloid and an attriting agent in a high moisture toothpaste composition. A toothpaste composition is prepared as described in Example 16 except that 0.5% MCC/CMC/CaCO$_3$, is used in place of the 0.5% AVICEL® PH 105. A toothpaste composition that has an initial viscosity of about 120,000 to about 140,000 cps is obtained. The toothpaste composition is stable when stored at 25° C. for six months.

Example 20

This example illustrates the use of colloidal microcrystalline cellulose co-processed with a surfactant in a high moisture toothpaste composition. A toothpaste composition is prepared as described in Example 16 except that 0.5% MCC/SLS is used in place of the 0.5% AVICEL® PH 105. A toothpaste composition that has an initial viscosity of about 120,000 to about 140,000 cps is obtained. The toothpaste composition is stable when stored at 25° C. for six months.

Examples 21 and 22

This example illustrates the use of colloidal microcrystalline cellulose co-processed with carrageenan in a high moisture toothpaste composition. A toothpaste composition is prepared as described in Example 16 except that 0.5% colloidal microcrystalline cellulose co-processed with carrageenan, such as is disclosed in Tuason, U.S. Pat. No. 6,391,368, is used in place of the 0.5% AVICEL® PH 105. A toothpaste composition that has an initial viscosity of about 120,000 to about 140,000 cps is obtained. The toothpaste composition is stable when stored at 25° C. for six months.

Similar results are obtained when colloidal microcrystalline cellulose co-processed with carrageenan, such as is disclosed in Tuason, WO 03/096976, is used in place of the 0.5% AVICEL® PH 105.

Example 23

This example illustrates the use of a mixture of microcrystalline cellulose and colloidal microcrystalline cellulose co-processed with carrageenan in a high moisture toothpaste composition. A toothpaste composition is prepared as described in Example 16 except that 0.25% colloidal microcrystalline cellulose co-processed with carrageenan, such as is disclosed in Tuason, U.S. Pat. Nos. 6,391,368, and 0.25% AVICEL® PH 105 is used in place of the 0.5% AVICEL® PH 105. A toothpaste composition that has an initial viscosity of about 120,000 to about 140,000 cps is obtained. The toothpaste composition is stable when stored at 25° C. for six months.

Similar results are obtained when 0.25% MCC/CMC/CaCO$_3$ and 0.25% AVICEL® PH 105 is used in place of the 0.5% AVICEL® PH 105, when 0.25% MCC/SLS and 0.25% AVICEL® PH 105 is used in place of the 0.5% AVICEL® PH 105, and when 0.25% colloidal microcrystalline cellulose co-processed with carrageenan, such as is disclosed in Tuason, WO 03/096976, and 0.25% AVICEL® PH 105 is used in place of the 0.5% AVICEL® PH 105.

Example 24 to 26

These examples illustrate the use of microcrystalline cellulose and co-processed colloidal microcrystalline cellulose in high moisture toothpaste compositions. Using the procedures described above, the toothpaste compositions shown in Table 11 were prepared and evaluated.

TABLE 11

HIGH MOISTURE TOOTHPASTE COMPOSITIONS

| Ingredient | Example 24 | Example 25 | Example 26 |
|---|---|---|---|
| TP 399 | 0.70 | 0.70 | 0.70 |
| 70% Sorbitol | 20.00 | 20.00 | 20.00 |
| Sodium saccharin | 0.20 | 0.20 | 0.20 |
| Methyl paraben | 0.08 | 0.08 | 0.08 |
| Propyl paraben | 0.02 | 0.02 | 0.02 |
| ZEODENT ® 165 | 7.00 | 7.00 | 7.00 |
| ZEODENT ® 113 | 9.00 | 9.00 | 9.00 |
| AVICEL ® PH 105 | 0.50 | 0 | 0 |
| AVICEL ® CL 611 | 0 | 0.50 | 0 |
| AVICEL ® RC 591 | 0 | 0 | 0.50 |
| Flavoring | 1.00 | 1.00 | 1.00 |
| SLS | 2.00 | 2.00 | 2.00 |
| Water | 59.50 | 59.50 | 59.50 |
| Moisture Content | 65.5 | 65.5 | 65.5 |
| Viscosity (Initial)/Cubans | 158,000/5 | 160,000/6 | 160,000/7 |
| Viscosity (1 Day)/Cubans | 160,000/5 | 151,000/7 | 151,000/7 |
| Stability (12 weeks - 25° C.) | | | |
| Viscosity cps/Cubans | 138,000/7 | 140,000/7 | 149,000/7 |

Example 27

This example illustrates the use of colloidal microcrystalline cellulose co-processed with a hydrocolloid and an attriting agent in a high moisture toothpaste composition. A toothpaste composition is prepared as described in Example 24 except that 0.5% MCC/CMC/CaCO$_3$, is used in place of the 0.5% AVICEL® PH 105. A toothpaste composition that has an initial viscosity of about 150,000 to about 160,000 cps is obtained. The toothpaste composition is stable when stored at 25° C. for twelve weeks.

Example 28

This example illustrates the use of colloidal microcrystalline cellulose co-processed with a surfactant in a high moisture toothpaste composition. A toothpaste composition is prepared as described in Example 24 except that 0.5% MCC/SLS is used in place of the 0.5% AVICEL® PH 105. A toothpaste composition that has an initial viscosity of about 150,000 to about 160,000 cps is obtained. The toothpaste composition is stable when stored at 25° C. for twelve weeks.

Example 29 and 30

This example illustrates the use of colloidal microcrystalline cellulose co-processed with carrageenan in a high moisture toothpaste composition. A toothpaste composition is prepared as described in Example 24 except that 0.5% of colloidal microcrystalline cellulose co-processed with carrageenan, such as is disclosed in Tuason, U.S. Pat. No. 6,391,368, is used in place of the 0.5% AVICEL® PH 105. A toothpaste composition that has an initial viscosity of about 150,000 to about 160,000 cps is obtained. The toothpaste composition is stable when stored at 25° C. for twelve weeks.

Similar results are obtained when colloidal microcrystalline cellulose co-processed with carrageenan, such as is disclosed in Tuason, WO 03/096976, is used in place of the 0.5% AVICEL® PH 105.

Example 31

This example illustrates the use of a mixture of microcrystalline cellulose and colloidal microcrystalline cellulose co-processed with carrageenan in a high moisture toothpaste composition. A toothpaste composition is prepared as described in Example 24 except that 0.25% colloidal microcrystalline cellulose co-processed with carrageenan, such as is disclosed in Tuason, U.S. Pat. No. 6,391,368, and 0.25% AVICEL® PH 105 is used in place of the 0.5% AVICEL® PH 105. A toothpaste composition that has an initial viscosity of about 150,000 to about 160,000 cps is obtained. The toothpaste composition is stable when stored at 25° C. for twelve weeks.

Similar results are obtained when 0.25% MCC/CMC/CaCO$_3$ and 0.25% AVICEL® PH 105 is used in place of the 0.5% AVICEL® PH 105, when 0.25% MCC/SLS and 0.25% AVICEL® PH 105 is used in place of the 0.5% AVICEL® PH 105, and when 0.25% colloidal microcrystalline cellulose co-processed with carrageenan, such as is disclosed in Tuason, WO 03/096976, and 0.25% AVICEL® PH 105 is used in place of the 0.5% AVICEL® PH 105.

Example 32

This example illustrates the use of a kappa-carrageenan in a high moisture toothpaste composition with silica.

TABLE 12

| Ingredient | % by weight |
|---|---|
| 70% Sorbitol | 60.00 |
| Kappa-carrageenan | 0.28 |
| CMC | 0.27 |
| Sodium saccharin | 0.20 |
| Sodium benzoate | 0.20 |
| Titanium dioxide | 0.50 |
| ZEODENT ® 165 | 7.00 |
| AVICEL ® PH 102 | 10.00 |
| Flavor | 1.00 |
| Water | 20.55 |
| Moisture Content | 38.55 |

TABLE 12-continued

| Time | Cuban Value |
|---|---|
| Initial | 2 |
| 1 Day | 3 |
| 6 Weeks | 9 |
| 9 Weeks | 8 |

It this toothpaste composition AVICEL® PH 105 microcrystalline cellulose could be used instead of AVICEL® PH 102 microcrystalline cellulose.

Examples 33 and 34

This example illustrates the use of a mixture of xanthan and carboxymethyl cellulose in high moisture toothpaste compositions.

TABLE 13

SILICA-BASED TOOTHPASTES CONTAINING CARRAGEENAN

| Ingredient | Example 33 | Example 34 |
|---|---|---|
| TPP 399 | 0.90 | 0.70 |
| 70% Sorbitol | 15.00 | 15.00 |
| Sodium benzoate | 0.20 | 0.20 |
| Saccharin | 0.20 | 0.20 |
| ZEODENT® 165 | 7.00 | 7.00 |
| ZEODENT® 113 | 7.00 | 9.00 |
| MCC | 0 | 0 |
| Flavoring | 1.00 | 1.00 |
| SLS | 2.00 | 2.00 |
| Water | 66.7 | 64.9 |
| Moisture Content | 71.2 | 69.4 |
| Viscosity | | |
| Viscosity - Initial cps/Cubans | 153,000/8 | 135,000/5 |
| Viscosity - 1 day - Cubans | Lumpy | 5 |

Examples 35 to 40

These examples illustrate the high moisture toothpastes that comprise chalk (calcium carbonate) as the abrasive and carboxymethyl cellulose as the binder.

TABLE 14

TOOTHPASTES CONATINING CALCIUM CARBONATE

| Ingredient | Example 35 | Example 36 |
|---|---|---|
| CMC | 1.30 | 1.30 |
| 70% Sorbitol | 20.00 | 20.00 |
| Sodium saccharin | 0.15 | 0.15 |
| Sodium benzoate | 0.50 | 0.50 |
| Chalk | 40.00 | 40.00 |
| ZEODENT® 165 | 3.00 | 1.50 |
| MCC | 0 | 1.00 |
| Flavor | 1.00 | 1.00 |
| SLS | 1.80 | 1.80 |
| Water | 32.25 | 37.75 |
| Moisture Content | 38.25 | 43.75 |
| Viscosity | | |
| Viscosity - Initial - Cubans | 2 | 4 |
| Viscosity - 1 day - Cubans | 6 | 4 |

TABLE 15

TOOTHPASTES CONATINING CALCIUM CARBONATE

| Ingredient | Example 37 | Example 38 |
|---|---|---|
| CMC | 1.30 | 1.30 |
| 70% Sorbitol | 15.00 | 15.00 |
| Sodium saccharin | 0.15 | 0.15 |
| Sodium benzoate | 0.50 | 0.50 |
| Chalk | 40.00 | 40.00 |
| ZEODENT® 165 | 3.00 | 1.50 |
| MCC | 0 | 1.00 |
| Flavor | 1.00 | 1.00 |
| SLS | 1.80 | 1.80 |
| Water | 37.25 | 37.75 |
| Moisture Content | 41.75 | 42.25 |
| Viscosity | | |
| Viscosity - Initial - Cubans | 2 | 4 |
| Viscosity - 1 day - Cubans | 4 | 4 |

TABLE 16

TOOTHPASTES CONATINING CALCIUM CARBONATE

| Ingredient | Example 39 | Example 40 |
|---|---|---|
| CMC | 2.00 | 2.00 |
| 70% Sorbitol | 20.00 | 15.00 |
| Sodium saccharin | 0.15 | 0.15 |
| Sodium benzoate | 0.50 | 0.50 |
| Chalk | 40.00 | 40.00 |
| ZEODENT® 165 | 0 | 0 |
| MCC | 0 | 0 |
| Flavor | 1.00 | 1.00 |
| SLS | 2.00 | 2.00 |
| Water | 34.35 | 39.35 |
| Moisture Content | 40.35 | 43.85 |
| Viscosity | | |
| Viscosity - Initial - Cubans | 2 | 2 |
| Viscosity - 1 day - Cubans | 7 | 5 |

Having described the invention, we now claim the following and their equivalents.

What is claimed is:

1. A toothpaste composition comprising:
a binder; a surface active agent; an abrasive; a humectant; microcrystalline cellulose; and water; in which:
the abrasive is silica and said microcrystalline cellulose is non-colloidal microcrystalline cellulose, the composition additionally comprises a silica thickener, and the composition comprises 1 to 7 wt % of the silica thickener, less than 15 wt % of the silica abrasive, 45 to 64.5 wt % water, 0.8 to 3 wt % of the surface active agent; 0.05 to 3.0 wt % of the binder, and 0.1 to 8.0 wt % of the microcrystalline cellulose; wherein said composition has an as made viscosity of 120,000 to 155,000 cp.

2. The composition of claim 1 in which the composition comprises 50 to 64.5 wt % water.

3. The composition of claim 1 in which the composition comprises 60 to 64.5 wt % water.

4. The composition of any of claims 1, 2, or 3 in which the binder is selected from the group consisting of carrageenan, cellulose gums, and xanthan.

5. The composition of any of claims 1, 2, or 3 in which the composition additionally comprises 0.2 to 4.0 wt % of non-colloidal microcrystalline cellulose, colloidal microcrystalline cellulose, or a mixture thereof.

6. The composition of claim 1 in which the composition additionally comprises a flavoring and a sweetener.

7. The composition of claim 4 in which the composition additionally comprises a flavoring and a sweetener.

8. The composition of claim 5 in which the composition additionally comprises a flavoring and a sweetener.

* * * * *